United States Patent [19]

Tamborski et al.

[11] Patent Number: 4,640,833

[45] Date of Patent: Feb. 3, 1987

[54] USE OF PERFLUOROBROMOALKYL ETHERS AS X-RAY CONTRAST AGENTS

[75] Inventors: Christ Tamborski, Dayton; Leland C. Clark, Jr., Cincinnati, both of Ohio

[73] Assignees: Adamantech, Inc., Marcus Hook, Pa.; Children's Hospital Research Foundation, Cincinnati, Ohio

[21] Appl. No.: 710,931

[22] Filed: Mar. 11, 1985

Related U.S. Application Data

[63] Continuation of Ser. No. 470,343, Feb. 28, 1983, abandoned.

[51] Int. Cl.$^4$ .............................................. A61K 49/04
[52] U.S. Cl. ........................................................ 424/5
[58] Field of Search ............................................ 424/5

[56] References Cited

U.S. PATENT DOCUMENTS

| | | | |
|---|---|---|---|
| 3,453,333 | 7/1969 | Litt et al. ............................. | 260/614 |
| 3,778,381 | 12/1970 | Rosand et al. ....................... | 252/311 |
| 3,975,512 | 8/1976 | Long ..................................... | 424/5 |
| 4,285,928 | 8/1981 | Wada .................................... | 424/5 |
| 4,490,351 | 12/1984 | Clark .................................... | 424/5 |

OTHER PUBLICATIONS

Biochemistry Involving Carbon–Fluorine Bonds, edited by Robert Filler, ACS Symposium Series No. 28, 1976, Chapter 9.

"The Synthesis and Biological Screening of New and Improved Fluorocarbon Compounds for Use as Artificial Blood Substitutes".

*Primary Examiner*—Frederick E. Waddell
*Attorney, Agent, or Firm*—J. Edward Hess; Donald R. Johnson; Stanford M. Back

[57] ABSTRACT

Method of X-raying animals using as a contrast agent a perfluorobromoalkyl ether of the formula $C_mF_{2m+1}OC_nF_{2n}Br$ where m and n independently are integers of from 2 to 6, wherein the ether is used either neat or in an aqueous dispersion such as an emulsion.

6 Claims, No Drawings

USE OF PERFLUOROBROMOALKYL ETHERS AS X-RAY CONTRAST AGENTS

This application is a continuation of application Ser. No. 470,343, filed Feb. 28, 1983, now abandoned.

BACKGROUND OF THE INVENTION

This invention relates to the use of perfluorobromoalkyl ethers as X-ray radiopaque agents particularly in connection with radiation contrast imaging in animals, including humans. Radiopaque materials are useful, for example, in quantitating coronary artery occlusive disease, in stroke, and in other occlusive diseases.

Use of brominated fluorocarbons, such as perfluorooctyl bromide, as radiopaque materials has been reported in the article by D. M. Long, et al. entitled "Radiopaque Applications of Brominated Fluorocarbon Compounds in Experimental Animals and Human Subjects" appearing in *Biochemistry Involving Carbon-Fluorine Bonds,* edited by Robert Filler, ACS Symposium Series No. 28, 1976, pages 171-189.

U.S. Pat. Nos. 3,778,381 to Rosano et al and 3,453,333 to Litt et al describe perfluorohaloalkyl ethers related to the ether compounds of this invention.

SUMMARY

In accordance with the present invention it has been found that perfluorobromoalkyl ethers, as represented by perfluoro-1-bromobutylisopropyl ether, are excellent radiopaque materials. The ethers are stable to light and heat and are X-ray opaque. The ethers can be used neat or in aqueous dispersions, are relatively non-toxic, and transpire from mice at a good rate. In general, perfluoro chemicals having an ether linkage tend to be retained for very long periods in the RES reticuloendothelial system ("RES") of animals. The perfluorobromoalkyl ethers, however, have been found to transpire rapidly through the lungs, indicating that they are not retained in tissues as are other ethers.

DETAILED DESCRIPTION

The perfluorobromoalkyl ethers may be represented by the formula (I):

$$C_mF_{2m+1}OC_nF_{2n}Br \qquad (I)$$

where n and m independently are integers of 2 to 6. Thus the ethers may contain from 4 to 12 carbon atoms as straight or branched chain alkyl groups. Such ethers are RES-phobic, i.e., they will leave or will not be retained by the reticuloendothelial system of the body. Specific ethers within the scope of formula I include:
F-1-bromoethylethyl ether
F-1-bromoethylisopropyl ether
F-1-bromopropylisopropyl ether
F-1-bromobutylisopropyl ether
F-1-bromobutylethyl ether
F-1-bromobutylpentyl ether
F-1-bromohexylisopropyl ether Generally, the ether can be prepared from an iodide precursor. For example, perfluoro-1-bromobutylisopropyl ether is readily prepared from perfluoro-1-iodobutylisopropyl ether by a free radical halogen exchange with bromine in the presence of ultraviolet (actinic) light as follows:

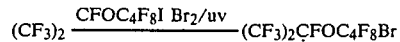

$$(CF_3)_2 \xrightarrow{CFOC_4F_8I \ Br_2/uv} (CF_3)_2CFOC_4F_8Br$$

The foregoing reaction gives an essentially quantitative conversion of the iodide compound to the desired bromide. Preparation of various iodide ether precursors and other methods of conversion to the bromides are disclosed, for example, in U.S. Pat. Nos. 3,453,333, 3,470,256 and 3,547,861 and in "Formation of Fluorinated Ethers in a Modified Halohydrin Reaction", Journal of Organic Chemistry, Vol. 33, No. 5, May, 1968, pages 1839-1844. Use of $(CF_3)_2CFOC_4F_8I$ to prepare other ethers is disclosed in U.S. Pat. Nos. 3,790,607, 3,781,370 and 3,637,868.

The ethers will vary somewhat in their radiopacity; those ethers having higher bromine to carbon weight ratios will exhibit greater contrast. The higher bromine content ethers, having fewer carbon atoms, will be less expensive to synthesize. However, the lower carbon content ethers, such as perfluoro-1-bromoethylisopropyl ether, $(CF_3)_2CFOC_2F_4Br$, also have higher vapor pressures and therefore will transpire more rapidly from animals. Accordingly, the selection of an ether for use in a particular radiopaque application will depend upon how much contrast is required, how quickly it is desired to have the ether leave the body and, of course, how toxic the ether is to the animal. With respect to toxicity, some toxicity may be tolerable by the animal; hence, while a totally non-toxic material is preferred, a lower level of toxicity may be acceptable depending on the species of animal, the state of health of the animal, and other considerations of a pharmacological nature.

Since the perfluorobromoalkyl ethers are also good oxygen and carbon dioxide carriers, they can double as blood substitutes when suitably emulsified or dispersed in an aqueous medium or can be admixed with other perfluorocarbon blood substitutes, in the manner described in U.S. Pat. Nos. 3,911,138 and 4,105,798 and other blood substitute literature. Moreover, the ethers are highly miscible with or are good solvents for perfluorocarbon blood substitutes (such as those of the aforementioned patents) and therefore can be used as diluents for other perfluorocarbon blood substitutes or as solvents for perfluorocarbon blood substitutes which are normally solids.

The ethers can be used neat or mixed with water to form aqueous dispersions such as emulsions. Water emulsions of the oil-in-water or water-in-oil type may be used. The greater the amount of perfluorobromoalkyl ether, the greater the opacity. The emulsions can contain about 10% to about 90% by volume of water, preferably 50-90% by volume, and the perfluorobromoalkyl ether may comprise as high as about 95% by volume and as low as about 5% by volume of the emulsion, preferably about 5-20% by volume. Mixtures of different ethers can be used. Normally, the emulsion will contain about 0.5-10% by weight, preferably 1-5% by weight, of an emulsifier based on the water content of the emulsion. The specific emulsifier employed is not critical, but it should itself be non-toxic or the toxicity should be tolerable, and it should form a relatively stable emulsion. Preferred emulsifiers are the non-ionic types, such as yolk phospholipid, a surfactant known to be harmless to humans. Also suitable are the polyoxyethylenes, polyoxypropylenes and copolymers thereof, available commercially under the "Pluronic"

trademark, and the fluorinated surfactants described in U.S. Pat. Nos. 3,828,085 and 3,547,995.

The perfluorobromoalkyl ether contrast agents of the invention can be used in a variety of radioimaging applications for medical and veterinary diagnostic purposes. Fields of radiographical use include, for example, gastroenterography, alveolography, bronchography, lymphography, ventriculomyelography, splenography, cholecystography, pancreatography, renal angiography and retrograde urography. With specific reference to renal angiography, the bromoethers of this invention, when employed for instance as emulsions, are unique in that they are not excreted in the urine. Moreover, all the arteries, arterioles, venules and veins of the kidney stand out very clearly. On the other hand, an x-ray made with a conventional iodinated, water soluble contrast agent provides a solid black, kidney-shaped silhouette because the agent is excreted so rapidly. In the case of lymphangiography, the known water soluble contrast agents are syrupy and therefore it is very difficult to use a tiny 30 gauge needle for their administration. The perfluorobromoalkyl ether contrast agents, however, go through such a needle very easily and, therefore, facilitate the diagnostic procedure.

When the ether, neat or as an aqueous dispersion, is used as a radiopaque agent, it can be introduced into the animal by various means. Suitable methods include swallowing, injection, and catheterization. The amount used can vary substantially depending in part on the weight of the animal, and the particular region being X-rayed. The intensity (or amount) of the X-ray irradiation can also influence the amount of ether used. The foregoing factors will routinely be taken into consideration by one skilled in the art to determine the effective amount for the condition being studied.

The ether or ether dispersion should be rendered isotonic or otherwise physiologically acceptable to the blood prior to introduction into the bloodstream by the addition of salts (e.g., as Ringer solution), buffering agents (such as $NaHCO_3$) or other additives commonly employed for such purpose.

The following example will further illustrate the invention without necessarily limiting the scope thereof, except as set forth in the appended claims.

EXAMPLE

Perfluoro-1-bromobutylisopropyl ether, $(CF_3)CFOC_4F_8Br$, is prepared in 85% yield by reacting bromine with $(CF_3)_2CFOC_4F_8I$ in the presence of ultraviolet light. The product is purified using a Perkin-Elmer Annular Still and preparative gas chromatography, and is characterized by mass spectrometry and infrared spectroscopy. The ether has a boiling point of 113°–115° C. at 760 torr and a density of 1.861 g/cc at 24° C. Molecular weight: 446 (calculated and found).

The ether has an LD-50 of over 100 mls/kg as an emulsion containing 10% by volume of the ether and 90% by volume of 5% by weight Pluronic F68 surfactant in water, and therefore is relatively non-toxic. The Pluronic F68 surfactant is a polyoxyethylene-polyoxypropylene copolymer having a molecular weight of about 8200. The limits of the toxicity data are as follows:

TABLE 1

| Emulsion Dose (ml/kg) | Number Alive at Time Shown | | |
|---|---|---|---|
| | 10 Min. | 1 Hour | 7 Days |
| 100 | 3/4 | 3/4 | 3/4 |

TABLE 1-continued

| Emulsion Dose (ml/kg) | Number Alive at Time Shown | | |
|---|---|---|---|
| | 10 Min. | 1 Hour | 7 Days |
| 75 | 4/4 | 4/4 | 4/4 |
| 50 | 4/4 | 4/4 | 4/4 |

To determine emulsion stability, the above-described emulsion of the ether, prepared by ultrasonication, is stored at 2° C. in a sealed Pyrex (trademark) tube in a refrigerator. Emulsion stability is determined by measurement of optical density initially and after several days storage of the samples using a Spectronic 20 apparatus and a suitable size cell. Comparison with emulsions in which perfluorodecalin or perfluorotributyl amine is substituted for the ether indicates that the ether emulsion is reasonably stable. Stability of other perfluorobrominated ether emulsions would be expected to vary.

Transpiration is measured by injecting a mouse with the test emulsion described above and placing the mouse in an all-glass chamber through which oxygen flows at a rate of about 20 cc per minute. After 20 minutes, samples of the oxygen are removed using a microsyringe and analyzed by gas chromatography using an SE-30 column and an electron capture detector. By calibration of the detector with a standard prepared from the perfluorocompound of the emulsion, the rate at which the perflouro compound is transpired through the skin and lungs of the intact, awake mouse can be calculated. Knowing the amount injected into the mouse and the rate at which it leaves over a period of time, the time at which all of the perfluoro compound would be gone can be calculated.

The results of the foregoing procedure, as compared with essentially the same emulsions except for use of different perfluoro compounds (perfluoro decalin and perfluorooctylbromide), expressed in terms of the rates (ug/min.) at which the perfluoro compound leaves the mouse at lapsed times of 5, 10, 20, 30 and 40 weeks, indicate that the perfluoro-1-bromobutylisopropyl ether leaves the body at a rate almost the same as perfluorodecalin (known to transpire quickly) and therefore has a desirable transpiration rate.

Accumulation of the perfluoro-1-bromobutylisopropyl ether in the liver and spleen of mice infused with the above-described ether emulsion is determined by direct combustion of liver and spleen homogenates by sodium biphenyl followed by fluoride ion measurement with an electrode. The results are as follows where the infusion dose is 100% cc/kg.

TABLE 2

| Wet Combustion Analysis of Liver and Spleen | | | |
|---|---|---|---|
| Days After Infusion | Percent of Dose Remaining | | |
| | Liver | Average | Spleen |
| 7 | 15.85 16.72 | 16.3 | 4.77 |
| 13 | 2.59 2.59 | 2.59 | 2.30 |
| 24 | 1.4 1.2 | 1.3 | 0.4 |

The data show that the ether went to the liver and spleen, and then left.

In other experiments, tissue samples are taken from mice which are given intravenous doses of the above-described emulsion containing the perfluoro-1- bromobutylisopropyl ether. The emulsion doses are 100, 75 and 50 cc/kg. The mice are sacrificed at 7, 13 and 24 days and samples of liver, spleen and kidney are removed, fixed and mounted for sectioning. Also, a sample of spleen is removed from a mouse at 330 days post-infusion. Some of these tissues are sectioned and examined. During the period when the ether is present in large amounts, microscopic examination reveals little or no mitosis of hepatocytes, but some hypertrophy of nuclei is seen. Binucleated cells are observed and in one case as many as 53% are binucleated. Less than 1% of hepatocyte cytoplasm is occupied by the perfluorobromoalkyl ether. Some infiltration of mononuclear cells is observed and blast-like cells as well as fluorocarbon particles are found in the interstitium. The re-emulsification of the larger fluorocarbon particles into smaller particles, which normally precedes the disappearance, is very near completion. By two weeks post-infusion, the liver is within normal limits with the exception of some phagocytes containing the perfluorobromo compound, and nuclei of hepatocytes are seen somewhat enlarged, but otherwise normal.

A neat sample of the perfluoro-1-bromobutylisopropyl ether is injected into the trachea of an anesthetized rat through a plastic tube having a bevelled end. Serial X-rays are taken and show the ether to be a good contrast agent. Similarly, the above-described emulsion containing the ether is intravenously injected into a mouse. X-rays (50 KVA applied) are taken two days later. The X-rays clearly show the liver and spleen, indicating that the ether is deposited in the reticuloendothelial system. The foregoing results thus demonstrate effective use of the ether as a radiopaque agent.

What is claimed is:

1. In a method of radioimaging an internal region of an animal wherein a radiopaque agent is introduced into the region and the region is X-rayed while perfused with the radiopaque agent, the improvement which comprises employing as the radiopaque agent a perfluorobromoalkyl ether of the formula:

$$C_mF_{2m+1}OC_nF_{2n}Br$$

where m and n independently are integers of from 2 to 6.

2. The method of claim 1 wherein the ether is F-1-bromobutylisopropyl ether.

3. The method of claim 1 wherein the radiopaque agent comprises an aqueous dispersion of the ether.

4. The method of claim 3 wherein the aqueous dispersion contains about 50–90% by volume of water, about 0.5–10% by weight of a dispersant based on the water content, and about 5–20% by volume of the ether.

5. The method of claim 1 wherein the agent is introduced into a lung.

6. The method of claim 5 wherein the agent is F-1-bromobutylisopropylether.